United States Patent [19]

Hsu

[11] Patent Number: 4,620,027
[45] Date of Patent: Oct. 28, 1986

[54] CATALYST AND PROCESS FOR PRODUCTION OF CINNAMATES

[75] Inventor: Chao-Yang Hsu, Media, Pa.

[73] Assignee: Sun Refining and Marketing Company, Philadelphia, Pa.

[21] Appl. No.: 684,766

[22] Filed: Dec. 21, 1984

[51] Int. Cl.$^4$ ............................................. C07C 69/76
[52] U.S. Cl. .................... 560/104; 562/406; 560/75; 560/20; 560/55; 560/59
[58] Field of Search ............... 560/104, 75, 20, 55, 560/59; 562/406, 400

[56] References Cited

U.S. PATENT DOCUMENTS 3,346,625 10/1967 Fenton et al. .................. 562/406
3,381,030 4/1968 Biale ............................. 562/406
3,437,676 4/1969 von Kutepow ................. 562/406
3,530,168 9/1976 Biale ............................. 562/406

FOREIGN PATENT DOCUMENTS 7021342 2/1982 Japan ............................. 560/104

Primary Examiner—Paul J. Killos
Attorney, Agent, or Firm—J. Edward Hess; Donald R. Johnson; Stanford M. Back

[57] ABSTRACT

A method of preparing esters of cinnamic acid comprising catalytically reacting a styrene compound with carbon monoxide, oxygen, and an aliphatic alcohol. The catalyst is a combination of a palladium (II) compound, an alkali metal carboxylate and a copper salt.

13 Claims, No Drawings

CATALYST AND PROCESS FOR PRODUCTION OF CINNAMATES

BACKGROUND OF THE INVENTION

The present invention relates to a catalytic process for preparing cinnamates by oxidative carbonylation of styrene compounds.

Cinnamic acid and cinnamates are used as a material for perfumes, as a cinnamic aldehyde, cyclamen aldehyde, beta-amyl cinnamic aldehyde, and the like.

Cinnamates are made conventionally through a Claisen condensation from benzaldehyde and alkylacetate in the presence of sodium alkoxide, as shown in Equation I

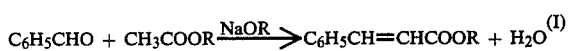

Another method of making cinnamates is by esterification of cinnamic acid, as shown in Equation II $$C_6H_5CH=CHOOH + ROH \rightarrow C_6H_5CH=CHCOOR + H_2O \quad (II)$$

Recently, several methods for preparing cinnamates have been reported, employing palladium catalysts. Heck et al., J. Amer. Chem. Soc. 91, 6707 (1969) and Patel et al., J. Org. Chem., 42, 3903 (1977), show methods of preparing cinnamates using palladium acetate-tertiary phosphine as a catalyst in the reaction of phenyl bromide and an alkyl acrylate. This reaction has the drawback of involving rather expensive raw materials. This reaction is shown in Equation III.

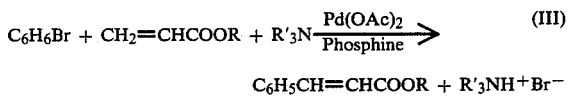

Other cinnamates such as methyl cinnamate, can be synthesized in a palladium catalyzed reaction by reacting styrene with carbon monoxide and methanol, as reported by J.K. Stille and his coworkers, J. Amer. Chem. Soc., 98, 1806 (1976) and 98, 1810 (1976); J. Org. Chem., 44, 3474 (1979); and by G. Cometti and G. P. Chiusoli in J. Organometal. Chem., 181, C14 (1979). In Stille's method, methyl cinnamate could be obtained only in a small amount, with dimethyl phenylsuccinate being the major product. Additionally, a stoichiometric amount of copper (II) salt was required in this reaction. The method of Cometti and Chiusoli has the same disadvantage of using a large excess of copper (II) salt as an oxidant Thus, both methods are unsuitable for industrial applications.

Many patents disclose oxidative carbonylation of olefins to alpha, beta-unsaturated esters by reacting an olefin with carbon monoxide, oxygen, and an alcohol in the presence of a catalytic amount of palladium and copper salts, cf. U.S. PAT. NOS. 3,381,030; 3,397,225; 3,397,226; 3,530,168; 3,621,054. None of these patents discloses a satisfactory method for producing cinnamates.

Two Japanese patent applications, 21,342 (1982) and 21,343 (1982), disclose that low yields of methyl cinnamate could be achieved through oxidative carbonylation of styrenes, provided that an excess amount of dehydrating agent is used in the reaction. Because the dehydrating agent is an expensive component of the reaction, industrial application of this method is limited. It was disclosed in these two Japanese applications that when styrenes were allowed to react with aliphatic alcohols, carbon monoxide, and oxygen in the presence of palladium and a dehydrating agent, cinnamates could be obtained with a high reaction rate and a high yield. However, this reaction has the disadvantage of requiring an excess of dehydrating agent, which makes the reaction unfeasible for industrial use.

SUMMARY OF THE INVENTION

Cinnamates can be produced by the oxidative carbonylation of styrene compounds according to the following reaction, in the absence of dehydrating agent:

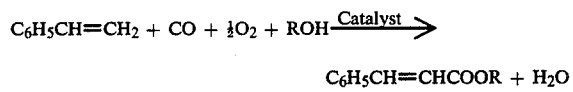

$$C_6H_5CH=CHCOOR + H_2O$$

It was unexpectedly found that when a styrene compound was reacted with carbon monoxide, oxygen, and an aliphatic alcohol and in the present of a catalytic amount of a palladium salt, an alkali metal salt of a carboxylic acid and a copper salt, high reaction rates and high yields of alkyl cinnamate could be obtained, along with valuable acetophenone as a byproduct. Moreover, unlike the prior art reactions, this reaction can be carried out smoothly either without any dehydrating agent or using only catalytic amounts of dehydrating agent to increase the reaction rate and total yield of the alkyl cinnamates.

The present invention relates to a method for the oxidative carbonylation of styrenes to alkyl cinnamates by reacting styrene compounds with carbon monoxide, oxygen, and aliphatic alcohols in the presence of a catalyst consisting of a palladium salt, an alkali metal salt of a carboxylic acid and a copper salt. The general formula for styrene compounds for use in the present invention can be represented by the following structure:

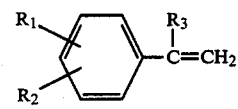

wherein $R_1$ and $R_2$ can be hydrogen, halogen, hydroxyl, alkyl, alkoxyl, aryl, aryloxy, or nitro functional groups. $R_3$ is hydrogen or an alkyl group of one to six carbon atoms. Specific examples for styrenes are styrene, alpha-methyl styrene, p-chloro styrene, p-nitro styrene, m-methoxy styrene, p-phenyl styrene, beta-methyl-p-isopropylstryene, beta-amylstyrene, and the like.

The aliphatic alcohols for use in the reaction according to the present invention include aliphatic alcohols having from one to six carbon atoms, such as methanol, ethanol, propanol, isopropanol, t-butanol, n-butanol, hexanol, and the like. It is also possible to use compounds capable of yielding the aforementioned alcohols in reaction systems containing acetals, ketals, orthoesters of carboxylic acids, dialkylcycloaklanes, orthoboric acid esters, and the like.

Carbon monoxide and oxygen for this reaction can be used either in the pure state or can be mixed with nitrogen, argon, and other inert gases as the diluents. Air can be used as the oxygen source. In general, carbon monoxide and oxygen can be charged into the reactor through a separated inlet system or can be charged as a mixture with or without inert gases as the diluents. The partial pressure of carbon monoxide or oxygen is adjusted so that the gas mixture in the reactor system is outside the explosive range.

The catalyst consists of three components, a palladium salt, an alkali metal salt of carboxylic acid (alkali metal carboxylate) and a copper salt. The palladium salt can be palladium chloride, palladium bromide, palladium iodide, palladium nitrate, or other divalent palladium salts such as palladium acetate, palladium benzoate, palladium acetylacetonate, palladium trifluoroacetate, palladium oxide, potassium tetrabromopalladate, sodium tetrachloropalladate, and the like. Any other forms of palladium which can form palladium (II) salt under the reaction conditions can be used. Examples are supported palladium such as palladium on carbon, palladium on silica, or palladium on alumina, palladium on silica-alumina, magnesia, titania, kieselguhr, active charcoal, graphite, etc., palladium black, and palladium sponge. Further examples of useful palladium compounds are palladium alpha-picolinate, carboxylates of divalent palladium, bis (acetylacetonato) palladium, bis (triphenylphosphine) dichloro palladium, cyclooctadiene dichloropalladium, tetramine dichloro palladium, and the like.

The alkali metal carboxylate can be a carboxylate of an alkali metal such as lithium, sodium, potassium, cesium, and rubidium. Specific carboxylic acids which can be ised to make the alkali metal salts for use in the present invention include the $C_1-C_{10}$ carboxylic acids, including straight and branched chain acids, and aromatic and $C_1-C_{10}$ alkyl aromatic acids as well as dicarboxylic acids having from one to 10 carbons in a straight or branched chain or aromatic and alkylaromatic dicarboxylic acids. Specific examples of alkali metal carboxylates for use in the present invention include the lithium, sodium, or potassium salts of acetic, propionic, butyric, valeric acids or dicarboxylic acids such as malic, malonic, succinic, or glutaric acid, or aromatic acids such as benzoic acid or phthalic acid.

The copper salts used in the reaction according to the present invention can be either copper (I) or copper (II) salts. Examples of these salts are copper (I) or (II) halides such as copper (II) fluoride, copper (I) chloride, copper (II) chloride, copper (I) bromide, copper (II) bromide, copper (I) iodide, and other non-halide copper salts such as copper (II) nitrate, copper (II) acetate, and copper (II) sulfate.

The reaction temperatures can range from about 25° to 250° C., and the preferred temperature range is from about 50° C. to about 150° C.

Reaction pressures can range from about 1 to about 1500 psi, although ranges in the amount of about 50 to about 750 psi are preferred.

The gas composition, the molar ratio of carbon monoxide to oxygen, can range broadly from about 0.1 to 20. A molar ratio of carbon monoxide to oxygen of from about 0.25 to 10 is preferred.

The catalyst composition can range from a molar ratio of copper to palladium of about 1 to 50, although a molar ratio of copper to palladium of about 2.5 to 20 is preferred.

The alkali metal carboxylate is present in the catalyst composition in a molar ratio of alkali metal to palladium of about 1 to 100 although a molar ratio of alkali metal to palladium of about 2.5 to 40 is preferred.

The molar ratio of styrene compound to palladium can range from about 10,000 to 10. A molar ratio of styrene to palladium of about 1000 to 25 is preferred.

The molar ratio of alcohol to styrene can range from 500 to 1, although a molar ratio of alcohol to styrene compound of form about 10 to about 1 is preferred.

It has been found that the use of alkali metal carboxylates as catalytic materials in the reaction according to the present invention greatly increases the selectivity of the reaction over and above the selectivity found with the use of any other types of compounds. The use of the alkali metal carboxylates has been found useful in reactions according to the present invention where it is desired to increase the amount of cinnamic acid ester produced to the detriment of production of acetophenone or other undesirable reaction products.

DETAILED DESCRIPTION OF THE INVENTION

The following examples represent specific methods of producing cinnamates according to the present invention.

EXAMPLE I

Styrene (54.0g, 483 mmole), methanol (78.4 g, 2246 mmole), palladium (II) chloride (0.444 g, 2.5 mmole), sodium propionate (2.4 g, 25.0 mmole) and copper (I) bromide (3.586 g, 25 mmole) were charged into a 300 ml Hastelloy autoclave. After the autoclave was sealed, it was purged with a gas mixture containing 12% carbon monoxide in air by bubbling the gas mixture through the liquid contents of the autoclave while stirring for about 10 minutes. After that, the gas flow was adjusted to a 500 ml/min. flow rate, and the pressure in the reactor was adjusted to 500 psig with a back pressure regulator. The autoclave was then heated to 100° C., and the reaction was kept at this temperature for 3.0 hours.

After the reaction had gone to completion, the autoclave was cooled and the pressure was released. The reaction mixture was then analyzed using gas chromatography. Analysis of the reaction mixture showed the following composition: 96.1 mmole of styrene, 40.8 mmole, 91.8 mmole of acetophenone, 289.7 mmole of methyl cinnamate, and 3.6 mmole of dimethylphenylsuccinate. This corresponds to 80,1% conversion of styrene and 74.8% selectivity to methyl cinnamate.

EXAMPLE II

This example illustrates that the addition of a dehydrating agent such as 2,2-dimethoxypropane has little effect on the oxidative carbonylation of styrenes to cinnamates.

Example I was repeated with the addition of 2,2-dimethoxypropane (20.2g, 193.8 mmole). After the reaction, the following materials were obtained from gas chromatographic analysis: styrene, 102.7 mmole; acetophenone, 57.8 mmole; methyl cinnamate, 267.4 mmole; dimethyl phenyl succinate, 4.0 mmole. This corresponds to 77.1% conversion of styrene and 77.5% selectivity to methyl cinnamate.

EXAMPLES III-XI

In these examples, summarized in Table I, the reaction procedure is similar to that shown in Example I. Differences occur in the variation of reaction temperature, pressure, time, and catalyst composition.

TABLE I

|  | EXAMPLE 3 | EXAMPLE 4 | EXAMPLE 5 | EXAMPLE 6 | EXAMPLE 7 | EXAMPLE 8 | EXAMPLE 9 | EXAMPLE 10 | EXAMPLE 11 |
|---|---|---|---|---|---|---|---|---|---|
| REAGENTS (mmole) | | | | | | | | | |
| Ph—CH=CH$_2$ | 477.7 | 475.8 | 459.6 | 497.7 | 463.0 | 496.2 | 514.9 | 502.3 | 493.4 |
| CH$_3$OH | 2246 | 2425 | 2470 | 2450 | 2444 | 2500 | 2499 | 2454 | 2474 |
| PdCl$_2$ | 2.5 | 2.5 | 2.5 | 2.5 | 2.5 | 2.5 | 2.5 | 2.5 | 2.5 |
| CuBr | 25.0 | 25.0 | 25.0 | 25.0 | 25.0 | 25.0 | 25.0 | 25.0 | 25.0 |
| C$_2$H$_5$COONa | 25.0 | 25.0 | 25.0 | 25.0 | 25.0 | 50.0 | 12.5 | 6.25 | 25.0 |
| CONDITIONS | | | | | | | | | |
| T (°C.) | 100 | 80 | 120 | 120 | 120 | 120 | 120 | 120 | 120 |
| P (psig) | 500 | 500 | 500 | 250 | 125 | 250 | 250 | 250 | 250 |
| t (min) | 180 | 300 | 240 | 240 | 240 | 240 | 240 | 210 | 240 |
| Gas Flo (ml/min) (12% CO in air) | 500 | 500 | 500 | 500 | 500 | 500 | 500 | 500 | 550 |
| RESULTS (mmole) | | | | | | | | | |
| Ph—CH=CH$_2$ | 96.1 | 83.0 | 52.0 | 37.5 | 145.9 | 168.0 | 13.0 | 77.2 | — |
| Ph—$\overset{O}{\overset{\|}{C}}$CH$_3$ | 40.8 | 20.5 | 30.8 | 21.9 | 63.4 | 48.5 | 27.0 | 1.4 | 78.8 |
| Ph—CH=CHCOOCH$_3$ | 289.7 | 280.4 | 356.7 | 430.1 | 183.6 | 193.4 | 461.5 | 312.1 | 253.8 |
| Ph—CHCH$_2$COOCH$_3$<br>     \|<br>    COOCH$_3$ | 3.6 | 63.0 | 3.4 | 2.5 | 3.2 | — | 0.5 | 9.0 | 1.9 |
| % CONVERSION OF STYRENE | 80.1 | 82.6 | 88.7 | 92.5 | 68.5 | 66.1 | 97.5 | 84.6 | 100 |
| % SELECTIVITY TO CINNAMATE | 74.8 | 71.3 | 87.5 | 86.4 | 58.0 | 59.0 | 91.9 | 73.4 | 71.7 |

EXAMPLES XII–XVII

TABLE II

|  | EXAMPLE 12 | EXAMPLE 13 | EXAMPLE 14 | EXAMPLE 15 | EXAMPLE 16 | EXAMPLE 17 |
|---|---|---|---|---|---|---|
| REAGENTS (mmole) | | | | | | |
| Ph—CH=CH$_2$ | 496.8 | 502.2 | 502.2 | 499.1 | 498.4 | 492.5 |
| CH$_3$OH | 2453 | 2450 | 2475 | 2463 | 2491 | 2483 |
| PdCl$_2$ | 2.5 | 2.5 | 2.5 | 2.5 | 2.5 | 2.5 |
| Cu Salt | CrBr, 25.0 | CuBr, 25.0 | CuCl 25.0 | CuCl$_2$, 25.0 | FeCl$_3$, 25.0 | CuBr, 25.0 |
| Sodium Carboxylate | Naprop, 12.5 | Naprop, 12.5 | Naprop, 12.5 | Naprop, 12.5 | Naprop, 12.5 | NaBu**, 12.5 |
| CONDITIONS | | | | | | |
| T (°C.) | 120 | 120 | 120 | 120 | 120 | 120 |
| P (psig) | 75 | 150 | 150 | 150 | 150 | 150 |
| t (min) | 240 | 240 | 240 | 240 | 240 | 210 |
| Gas Flow (ml/min) | CO:30<br>AIR:220 | CO:60<br>AIR:440 | CO:60<br>AIR:440 | CO:60<br>AIR:440 | CO:60<br>AIR:440 | 500*** |
| RESULTS (mmole) | | | | | | |
| Ph—CH=CH$_2$ | 238.7 | 95.3 | 17.4 | 50.4 | 95.8 | 17.0 |
| Ph—$\overset{O}{\overset{\|}{C}}$CH$_3$ | 16.2 | 13.4 | 35.9 | 151.2 | 117.3 | 27.5 |
| Ph—CH=CHCOOCH$_3$ | 162.8 | 386.5 | 423.3 | 160.6 | 130.1 | 411.2 |
| Ph—CHCH$_2$COOCH$_3$<br>     \|<br>    COOCH$_3$ | 11.9 | 9.2 | 8.4 | 2.1 | — | 1.9 |
| % CONVERSION OF STYRENE | 52.0 | 81.0 | 96.5 | 89.8 | 80.8 | 96.5 |
| % SELECTIVITY TO CINNAMATE | 63.1 | 95.1 | 87.3 | 35.8 | 32.3 | 86.5 |

*Naprop = Sodium Propionate
**NaBu = Sodium Butyrate
***12% CO in Air

In these examples, summarized in Table II, the reaction procedure is similar to that shown in Example I. Differences occur in the variation of oxidant, alkali carboxylate, and the gas phase materials charged into the reactor. The gas phase materials (carbon monoxide and air) were changed, under desired pressure, by controlling the flow rate and through a separated inlet system.

What is claimed is:

1. A method for the production of alkyl esters of cinnamic acid comprising the oxidative carbonylation of a styrene compound with carbon monoxide, oxygen, and an aliphatic alcohol in the presence of a catalytic amount of a palladium salt, an alkali metal carboxylate and a copper salt.

2. The method of claim 1 wherein the aliphatic alcohol has from 1 to 6 carbon atoms.

3. The method of claim 1 wherein the styrene compound has the formula

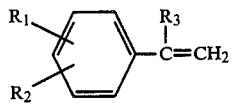

wherein $R_1$ and $R_2$ can be hydrogen, halogen, hydroxyl, alkyl, alkoxyl, aryl, aryloxyl, or nitro; and $R_3$ is hydrogen or an alkyl group of form 1 to 6 carbon atoms.

4. The method of claim 3 wherein the aliphatic alcohol has from 1 to 6 carbon atoms.

5. The method of claim 4 wherein the styrene is styrene.

6. The method of claim 5 wherein alcohol is methanol.

7. The method of claim 1 wherein the palladium salt is supported on a support selected from the group consisting of silica, silica-alumina, alumina, magnesia, titania, kieselguhr, active charcoal, and graphite.

8. The method of claim 1 wherein the palladium is supplied to the reaction in the form of palladium black.

9. The method of claim 1 wherein the palladium is supplied to the reaction in the form of palladium sponge.

10. The method of claim 1 wherein the copper salt is selected from the group consisting of copper (I) and copper (II) halides, copper (I) and copper (II) nitrates, copper (I) and copper (II) acetates, and copper (I) and copper (II) sulfates.

11. The method of claim 1 wherein the alkali metal carboxylate is selected from the group consisting of alkali metal salts of mono- and di- carboxylic acids having from one to ten carbon atoms, aromatic mono- and di- carboxylic acids, $C_1$–$C_{10}$ alkylaromatic mono- and di-carboxylic acids and mixtures thereof.

12. The method of claim 11 wherein the catalyst comprises palladium (II) chloride, sodium acetate, and copper (I) chloride.

13. The process of any of claims 1–12 wherein the oxidative carbonylation is carried out in the absence of a dehydrating agent.

* * * * *